United States Patent [19]

Taicher et al.

[11] Patent Number: 5,757,186

[45] Date of Patent: May 26, 1998

[54] NUCLEAR MAGNETIC RESONANCE WELL LOGGING APPARATUS AND METHOD ADAPTED FOR MEASUREMENT-WHILE-DRILLING

[75] Inventors: Gersh Zvi Taicher; Arcady Reiderman, both of Houston, Tex.

[73] Assignee: Western Atlas International, Inc., Houston, Tex.

[21] Appl. No.: 746,209

[22] Filed: Nov. 6, 1996

Related U.S. Application Data

[63] Continuation-in-part of Ser. No. 606,089, Feb. 23, 1996, Pat. No. 5,712,566.

[51] Int. Cl.$^6$ .................................................. G01V 3/14
[52] U.S. Cl. ............................................................ 324/303
[58] Field of Search ............................. 324/300, 303, 324/307, 309, 318; 175/45; 335/215, 219, 296, 302

[56] References Cited

U.S. PATENT DOCUMENTS

| | | | |
|---|---|---|---|
| 4,714,881 | 12/1987 | Givens | 324/303 |
| 4,717,876 | 1/1988 | Masi et al. | 324/303 |
| 4,717,877 | 1/1988 | Taicher et al. | 324/303 |
| 5,230,387 | 7/1993 | Waters et al. | 175/45 |
| 5,280,243 | 1/1994 | Miller | 324/303 |
| 5,557,201 | 9/1996 | Kleinberg et al. | 324/303 |

FOREIGN PATENT DOCUMENTS

0581666A2  2/1994  European Pat. Off. ......... G01V 3/32

OTHER PUBLICATIONS

Miller et al. Spin Echo Magnetic Resonance Logging: Porosity and Gree Fluid Index Determination. paper No. 20561. Society of Petroleum Engineers, Sep. 1990.

M.N.Miller et al. Spin Echo Magnetic Resonance Logging: Porosity and Free Fluid Index Determination, paper No. 20561. Society of Petroleum Engineers,Richardson, Texas 1990.

*Primary Examiner*—Sandra L. O'Shea
*Assistant Examiner*—Michael Eisenberg
*Attorney, Agent, or Firm*—Richard A. Fagin

[57] ABSTRACT

A nuclear magnetic resonance sensing apparatus including a magnet for inducing a static magnetic field in materials to be analyzed, the magnetic field having uniform field strength around, being substantially rotationally symmetric and perpendicular to a longitudinal axis of the magnet. The apparatus includes means for generating a radio frequency magnetic field in the materials to be analyzed. The radio frequency magnetic field is substantially rotationally symmetric about the longitudinal axis and is parallel to the longitudinal axis within a sensitive volume containing the materials to be analyzed. The apparatus includes means for receiving a nuclear magnetic resonance signal from the sensitive volume. In a preferred embodiment, the means for generating and means for receiving include an antenna coil wound so that turns of the coil lie in planes perpendicular to the longitudinal axis of the magnet.

23 Claims, 4 Drawing Sheets

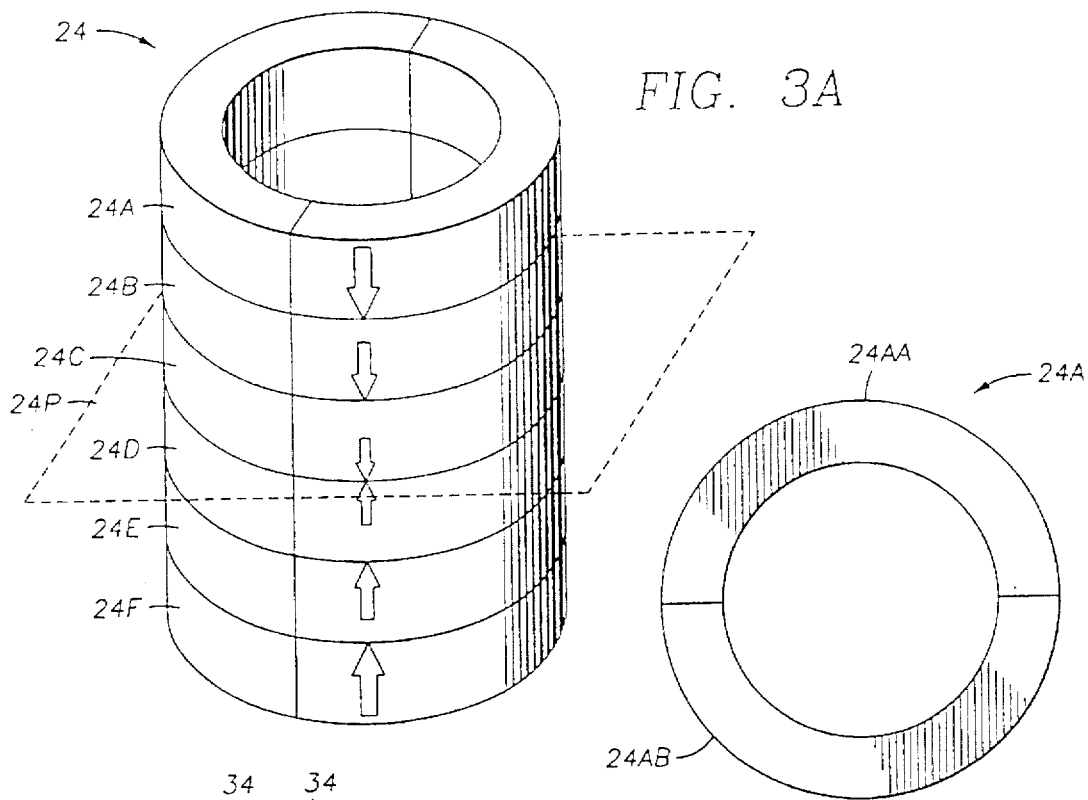
FIG. 3A
FIG. 3B
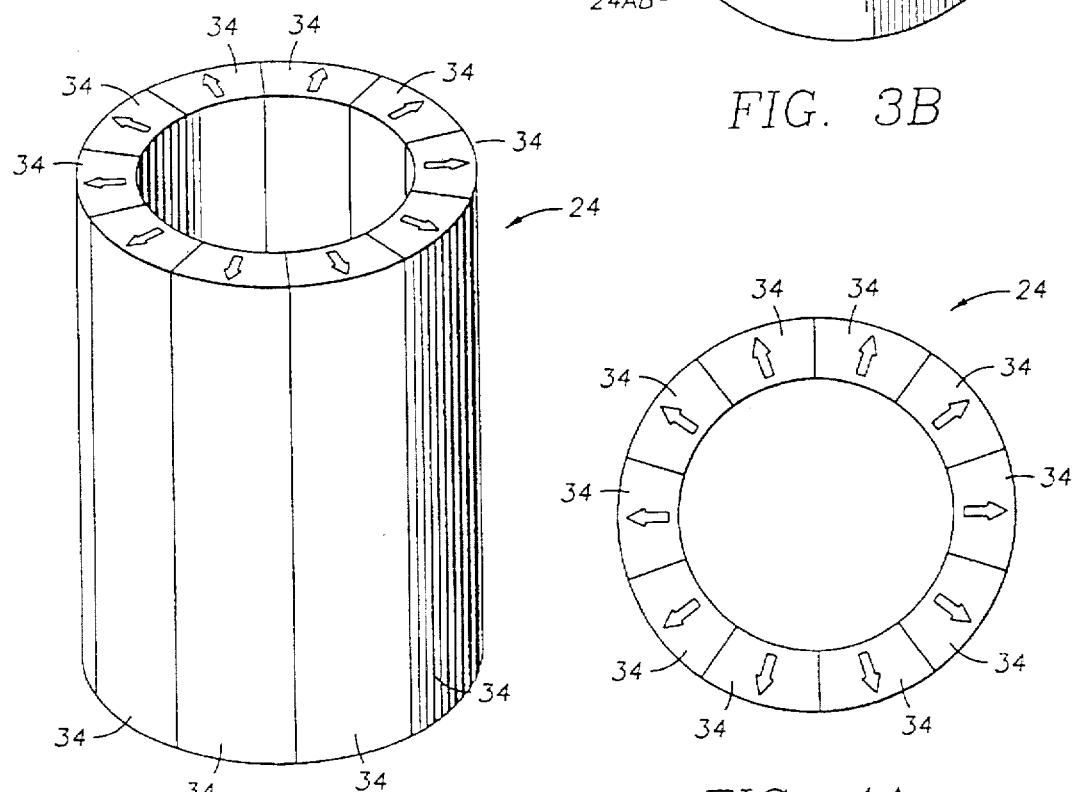
FIG. 4A
FIG. 4B

NUCLEAR MAGNETIC RESONANCE WELL LOGGING APPARATUS AND METHOD ADAPTED FOR MEASUREMENT-WHILE-DRILLING

CROSS REFERENCE TO RELATED APPLICATIONS

The present patent application is a continuation-in-part of Ser. No. 08/606,089 filed on Feb. 23, 1996, U.S. Pat. No. 5,712,566 entitled "Nuclear Magnetic Resonance Apparatus and Method".

BACKGROUND OF THE INVENTION

1. Field of the Invention

The present invention is related to the field of Nuclear Magnetic Resonance (NMR) sensing apparatus and methods. More specifically, the present invention is related to NMR well logging apparatus and methods for NMR sensing within a sensitive volume, particularly surrounding a wellbore penetrating earth formations. The present invention also relates to methods for using NMR measurements to determine properties of the earth formations surrounding the wellbore.

2. Description of the Related Art

NMR well logging instruments can be used for determining properties of earth formations including the fractional volume of pore space and the fractional volume of mobile fluid filling the pore spaces of the earth formations. Methods of using NMR measurements for determining the fractional volume of pore space and the fractional volume of mobile fluid are described, for example, in *Spin Echo Magnetic Resonance Logging: Porosity and Free Fluid Index Determination*, M. N. Miller et al, Society of Petroleum Engineers paper no. 20561, Richardson, Tex., 1990.

NMR well logging instruments known in the art typically make measurements corresponding to an amount of time for hydrogen nuclei present in the earth formations to substantially realign their spin axes, and consequently their bulk magnetization, either with an applied magnetic field or perpendicularly to the applied magnetic field, after momentary reorientation of the hydrogen nuclear spin axes by application of an orthogonal radio frequency (RF) magnetic field. The applied magnetic field is typically provided by a permanent magnet disposed in the NMR well logging instrument. The spin axes of hydrogen nuclei in the earth formation, in the aggregate, align with the magnetic field applied by the magnet. The NMR instrument also typically includes an antenna, positioned near the magnet and shaped so that a pulse of RF power conducted through the antenna induces the RF magnetic field in the earth formation. The RF magnetic field is generally orthogonal to the field applied by the magnet. This RF pulse, typically called a 90 degree pulse, has an amplitude and duration predetermined so that the spin axes of the hydrogen nuclei generally align themselves perpendicularly both to the orthogonal magnetic field induced by the RF pulse and to the magnetic field applied by the magnet. After the 90 degree pulse ends, the nuclear magnetic moments of the hydrogen nuclei gradually "relax" or return to their original alignment with the magnet's field. The amount of time taken for this relaxation is related to the properties of interest of the earth formation.

After the 90 degree pulse ends, the antenna is typically electrically connected to a receiver, which detects and measures voltages induced in the antenna by precessional rotation of the spin axes of the hydrogen nuclei. The precessional rotation generates RF energy at a frequency proportional to the strength of the magnetic field applied by the magnet, this frequency being referred to as the Larmor frequency. The constant of proportionality for the Larmor frequency is known as the gyromagnetic ratio ($\gamma_o$). The gyromagnetic ratio is unique for each different chemical elemental isotope. The hydrogen nuclei precess individually at different rates because of inhomogeneities in the magnet's field and because of differences in the chemical and magnetic environment within the earth formation. This process is referred to as dephasing. Differences in rates of precession of the spin axes of the hydrogen nuclei result in a rapid decrease in the magnitude of the voltages induced in the antenna. The rapid decrease in the induced voltage is referred to as the free induction decay (FID).

After a predetermined time period following the FID, another RF pulse is applied to the antenna. This RF pulse has an amplitude and duration predetermined to realign the spin axes of the hydrogen nuclei in the earth formation by an axial rotation of 180 degrees from their immediately previous orientations. After the end of this RF pulse (called a 180 degree pulse), hydrogen nuclear axes that were precessing at a slower rate are then positioned so that they are "ahead" of the faster precessing spin axes. The 180 degree reorientation of the nuclear spin axes therefore causes the faster precessing axes to be reoriented "behind" the slower precessing axes. The faster precessing axes then eventually "catch up" to, and come into approximate alignment with, the slower precessing axes after the 180 degree reorientation. As a large number of the spin axes thus become aligned with each other, the hydrogen nuclear axial precessions are again able to induce measurable voltages in the antenna. The voltages induced as a result of the rephasing of the hydrogen nuclear axes with each other after a 180 degree pulse are referred to as a "spin echo". The spin echo induced voltage is smaller than the original voltage generated after cessation of the first RF pulse, because the aggregate nuclear axial alignment, and consequently the bulk magnetization, of the hydrogen nuclei at the time of the spin echo is at least partially realigned with the magnet's field and away from the sensitive axis of the antenna. The spin echo voltage itself decays by FID as the faster aligning nuclear axes quickly "dephase" from the slower aligning nuclear axes.

After another period of time, typically equal to two of the predetermined time periods between the initial 90 degree RF pulse and the first 180 degree pulse, another RF pulse of the same duration as the 180 degree pulse is typically applied to the antenna. This next 180 degree pulse again causes the slower precessing spin axes to be positioned ahead of the faster precessing spin axes. Eventually another spin echo will occur and induce measurable voltages in the antenna. The induced voltages of this next spin echo will typically be smaller in amplitude than those of the previous spin echo.

Successive 180 degree RF pulses are applied to the antenna to generate successive spin echoes, each one typically having a smaller amplitude than the previous spin echo. The rate at which the peak amplitude of the spin echoes decays is related to properties of interest of the earth formations. The number of spin echoes needed to determine the rate of spin echo amplitude decay is related to the properties of the earth formation; in some cases as many as 1,000 spin echoes may be needed to determine the amplitude decay corresponding to the properties of the earth formation which are of interest.

Well logging instruments have lately been constructed within parts of an assembly used in the process of drilling wellbores with the purpose of making well logging measurements while the wellbore is being drilled. Such well logging instruments are known in the art as measurement-while-drilling (MWD) logging instruments. An MWD well logging instrument for making nuclear magnetic resonance (NMR) measurements is described, for example in U.S. Pat. No. 5,280,243 issued to Miller. The instrument disclosed in the Miller '243 patent includes a permanent magnet for inducing a static magnetic field in the earth formations surrounding the drilling assembly, a transceiver antenna disposed outside the magnet for inducing radio frequency (RF) magnetic fields in the formations and for receiving the NMR signal from excited nuclei in the earth formations.

A particular drawback to the apparatus disclosed in the Miller '243 patent is that the transceiver antenna and the magnet must have a substantial axial length relative to the diameter of a "sensitive volume" in order to maintain substantial rotational symmetry of the static and RF magnetic field amplitudes at substantial radial depth into the earth formations. The sensitive volume is the portion of the earth formation within which the nuclear magnetic resonance condition is generated by matching the RF frequency to the static magnetic field magnitude. In order to provide a sensitive volume at a radial distance from the instrument which is substantially disposed within the earth formation would require a very long magnet and antenna. A very long antenna, in particular, can reduce the vertical resolution so as to make the measurement commercially unacceptable. Further, MWD instruments are subject to severe shock and vibration. The instrument in the Miller '243 patent is particularly subject to excessive bending or even breakage of the portion of the drilling assembly where the magnet is located because the magnet is typically disposed on a portion of the drilling assembly having reduced external diameter to accommodate the magnet. The axial length required to have the requisite magnetic field symmetry in the Miller '243 apparatus may result in an unacceptably weak or flexible section of the drilling assembly.

Another drawback to the apparatus disclosed in the Miller '243 patent is that it is subject to error in making measurements particularly because the amplitudes of the static and RF magnetic fields are not fully symmetric about the axis of rotation of the apparatus. An MWD well logging apparatus, as part of the drilling assembly, is subject to being rotated in order to turn a drill bit typically mounted at the lower end of the drilling assembly. Rotational speeds can range as high as 200 RPM, and are more typically in the range of 60–120 RPM (1.0–2.0 revolutions/second). The NMR well logging instrument makes a series of spin echo measurements during a measurement cycle which is typically not less than ½ second in duration. During the measurement cycle, the apparatus may turn through ½ rotation or more. If the amplitudes of the static and RF magnetic fields are not fully rotationally symmetric, the measurement may be subject to significant error, particularly because certain parts of the sensitive volume will be located, after some rotation, within a different magnetic field strength which may be beyond the bandwidth of the receiver. That portion of the sensitive volume will therefore typically not contribute to the total signal amplitude.

Still another drawback to the apparatus described in the Miller '243 patent is that the directionality and relatively strong amplitude gradient of the static and RF magnetic fields causes the measurements made by the apparatus to be extremely sensitive to small radial displacements. U.S. Pat. No. 5,332,967 issued to Shporer describes the effect of even extremely small radial displacements on the measurements made by an apparatus configured as is the one disclosed in Miller '243. In particular, sideways shifts in the position of the magnet results in changes in the amplitude distribution of the static magnetic field, which in turn causes phase shifts in the nuclear magnetic precession. The phase shifts are of opposite polarity on opposite sides of the instrument the apparatus of the Miller '243 patent, which can lead to significant variations in NMR signal amplitude, or even complete loss of the NMR signal for even very small radial displacements of the instrument. Such small radial displacements are common for a well logging instrument, even one used in measurement-while-drilling applications.

The effect on NMR measurements of sideways motion of the instrument described in the Shporer '967 patent is also a problem for the apparatus disclosed in the Miller '243 patent. Even when the magnet is several feet long, the apparatus in Miller '243 can have several percent circumferential variation in the amplitude of the static magnetic field at any constant radius from the center of the instrument. When the apparatus disclosed in the Miller '243 patent is rotated, the small changes in field amplitude can cause a similar same phase shift error in the NMR signal measurement.

The problems of the Miller '243 apparatus are generally avoided by another NMR well logging apparatus described in U.S. Pat. No. 4,350,955 issued to Jackson et al. The Jackson et al '955 apparatus includes a pair of generally cylindrical magnets positioned coaxially and having like poles facing each other. The magnets generate a rotationally symmetric static magnetic field having a toroidal volume with substantially homogeneous magnetization. The magnet arrangement in Jackson et al '955 provides the rotational symmetry of the static magnetic field amplitude which is required to make rotating NMR measurements, but a particular drawback to the Jackson et al '955 apparatus is that the toroidal volume is typically too small in the axial direction to enable the NMR instrument to be used at commercially acceptable rates of axial motion ("rates of penetration" or "logging speeds") through the wellbore. During drilling of the wellbore, the drilling assembly and the instruments incorporated therein may move through the wellbore at speeds in excess of several inches per second. During the time needed to make the NMR measurements, an instrument configured according to Jackson et al '955 can move enough axially so that the NMR measurements are subject to substantial error.

An apparatus for NMR well logging disclosed by Clow et al in U.S. Pat. No. 4,629,986 has a magnet structure similar to that disclosed in Jackson et al '955, and therefore is subject to similar operational limitations as is the apparatus disclosed in Jackson et al '955.

Still another apparatus for NMR well logging is disclosed in U.S. Pat. No. 4,717,876 issued to Masi et al. The apparatus disclosed in Masi et al '876 includes a main magnet structure similar to that described in the Jackson et al '955 patent, but the Masi et al apparatus further includes radially magnetized annular cylindrical magnet sections disposed in the gap between the main magnets. The radially magnetized annular cylindrical magnet sections provide increased strength of the static magnetic field and a more homogeneous field strength when compared to the magnet structure of Jackson et al '955. The apparatus in Masi et al '876 still has a static field with only limited axial extent, and so is limited as to the rates of axial motion for which the instrument is commercially useful.

European Patent Office published application no. 0,581,666 A2 filed by Kleinberg et al and published on Feb. 2, 1994 discloses an NMR well logging apparatus for use in measurement-while-drilling (MWD) applications. The apparatus disclosed in the Kleinberg et al application is similar to the apparatus disclosed in Jackson et al '955, including two magnets positioned with like poles facing each other and an antenna coil disposed therebetween. The apparatus in the Kleinberg et al application, being structured substantially the same as the apparatus in Jackson et al '955 suffers substantially the same limitations as do all the other NMR-MWD well logging apparatus disclosed herein known in the art.

The NMR well logging apparatus disclosed in Masi et al '876, Jackson et al '955 and European Patent Office published application no. 0,581,666 A2 filed by Kleinberg et al are also subject to significant error in the measurements they make as a result of the structure of the static magnetic field induced by the magnets in each of these prior art apparatus. The static magnetic field induced by any of these prior art apparatus is typically shaped substantially as a toroid and has a substantially uniform magnetic field amplitude within the toroid. The frequency of the RF magnetic field is set to generate a nuclear magnetic resonance condition within the toroid, assuming the amplitude of the magnetic field within the toroid. The strength of the static magnetic field within the toroid is subject to variation caused by, among other things, the magnitude of the earth's magnetic field, and changes in the strength of the magnets as they are exposed to widely varying ambient temperatures present within the typical wellbore. If the static field amplitude within the toroid becomes such that the frequency of the RF field no longer generates a resonance condition substantially within the toroid, the NMR measurements thus made are subject to significant reduction in signal to noise ratio.

Accordingly, it is an object of the present invention to provide an NMR well logging apparatus which is particularly suited to be used as a measurement-while-drilling instrument which is capable of axial movement at commercially acceptable speeds.

It is another object of the present invention to provide an NMR well logging apparatus which is particularly suited to be used as a measurement-while-drilling instrument which is capable of being rotated while making accurate NMR measurements.

It is yet another object of the present invention to provide an NMR well logging apparatus which is particularly suited to be used as a measurement-while-drilling instrument which is not subject to significant reduction in signal to noise caused by changes in the strength of the static magnetic field or effects of the earth's magnetic field.

SUMMARY OF THE INVENTION

The present invention is a nuclear magnetic resonance sensing apparatus including a magnet for inducing a static magnetic field within materials to be analyzed. The static magnetic field is substantially rotationally symmetric around and perpendicular to a longitudinal axis of the magnet. The static magnetic field has substantially equal amplitude along the longitudinal axis. The apparatus includes a means for generating a radio frequency magnetic field in the materials to be analyzed. The radio frequency magnetic field is substantially rotationally symmetric about the longitudinal axis and is parallel to the longitudinal axis within a sensitive volume containing the materials to be analyzed. The apparatus includes means for receiving a nuclear magnetic resonance signal from the sensitive volume. In a preferred embodiment, the means for generating and means for receiving include an antenna coil wound so that turns of the coil lie in planes perpendicular to the longitudinal axis of the magnet.

In a particular embodiment of the invention, the magnet includes a radially magnetized cylinder disposed on a drill collar forming part of a drilling assembly.

The present invention includes a method for nuclear magnetic resonance measurement. The method of the present invention includes the steps of inducing a static magnetic field in the materials to be analyzed. The static magnetic field has substantially uniform field strength along a longitudinal axis and is substantially perpendicular to the longitudinal axis. The static magnetic field is also substantially rotationally symmetric about the longitudinal axis. The method includes generating a radio frequency magnetic field in the materials to be analyzed. The radio frequency magnetic field is substantially rotationally symmetric about the longitudinal axis and is substantially parallel to the longitudinal axis within a sensitive volume containing the materials to be analyzed. The method includes receiving a nuclear magnetic resonance signal from the materials to be analyzed.

In a specific embodiment of the invention, the method can be performed from an apparatus forming part of a drilling assembly.

BRIEF DESCRIPTION OF THE DRAWINGS

FIG. 3A shows a first embodiment of the magnet of the present invention.

FIG. 3B shows a top view of the magnet shown in FIG. 3A.

FIG. 4A shows a top view of a second embodiment of the magnet of the present invention.

FIG. 4B shows an oblique view of the magnet shown in FIG. 4A.

DESCRIPTION OF THE PREFERRED EMBODIMENT

Figure 1:
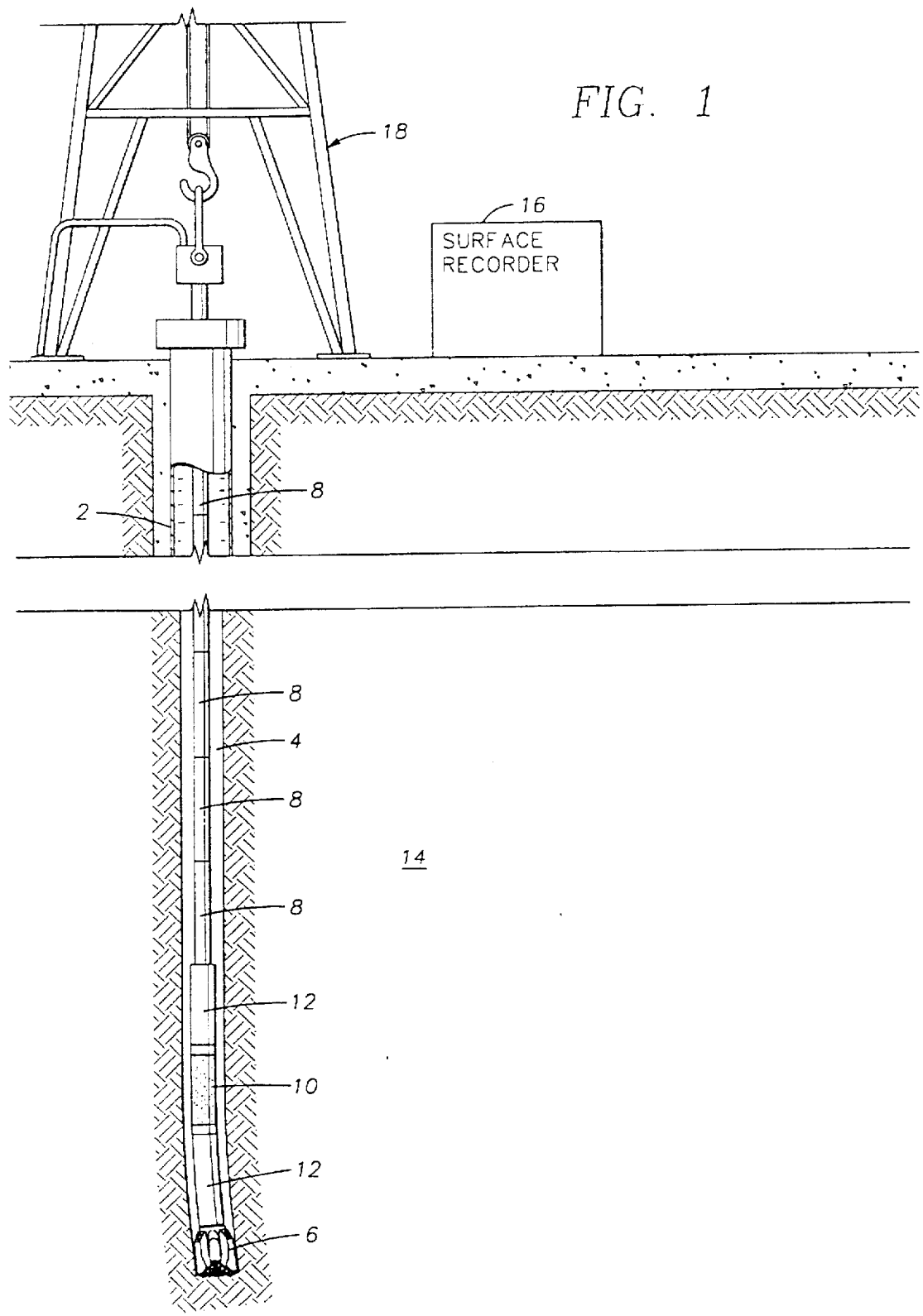
FIG. 1 shows a measurement-while-drilling (MWD) well logging instrument as it is typically used in the process of drilling a wellbore through earth formations.

A measurement-while-drilling (MWD) well logging instrument is shown in FIG. 1 as it is typically used in the process of measuring properties of earth formations during drilling of a wellbore 2. The instrument, shown generally at 10, is included as part of a drilling assembly. The drilling assembly typically includes a drill bit 6, heavy weight drill collars 12, and segmented drill pipe 8. The assembly can be lifted from and lowered into the wellbore 2, and can be rotated at the earth's surface by means of a drilling rig or similar surface apparatus, shown generally at 18. The drilling rig 18 typically includes pumping equipment (not shown separately for clarity of the illustration) for circulating a fluid 4 known as "drilling mud" through the interior of the drilling assembly and out into the wellbore 2 through the end of the drill bit 6. The drilling mud 4 is circulated to cool the bit 6 and to clear cuttings of earth formations 14 through which the bit 6 penetrates as it is turned and lowered further into the wellbore 2 while drilling.

The instrument 10 can include a pressure pulser (not shown) for modulating the pressure of the drilling mud 4 in accordance with a predetermined telemetry encoding scheme. The modulated drilling mud pressure can be detected and interpreted by a surface recorder 16, so as to reproduce and record at the earth's surface the measurements made by the instrument 10. Such telemetry and recording systems are well known in the art and are described, for example, in a sales brochure entitled "MWD Services". Integrated Drilling Services, Ltd., Aberdeen, Scotland AB1 4YA (1995). Alternatively, the instrument can include a digital memory (not shown separately in FIG. 1) or other internal data storage device for recording the various measurements made by the instrument 10 as is passes through the earth formations 14. The instrument 10 can obtain electrical operating power either through batteries (not shown) inserted in the instrument 10 or by a device, such as a rotary turbine, responsive to the flow of the drilling mud 4 through the interior of the instrument 10.

The configuration of the instrument 10 shown in FIG. 1 is intended to provide an overview of the conditions under which the instrument 10 operates, and is in no way meant to limit the number of or types of sensors which may be included in the MWD well logging instrument 10 of the present invention.

Figure 2:
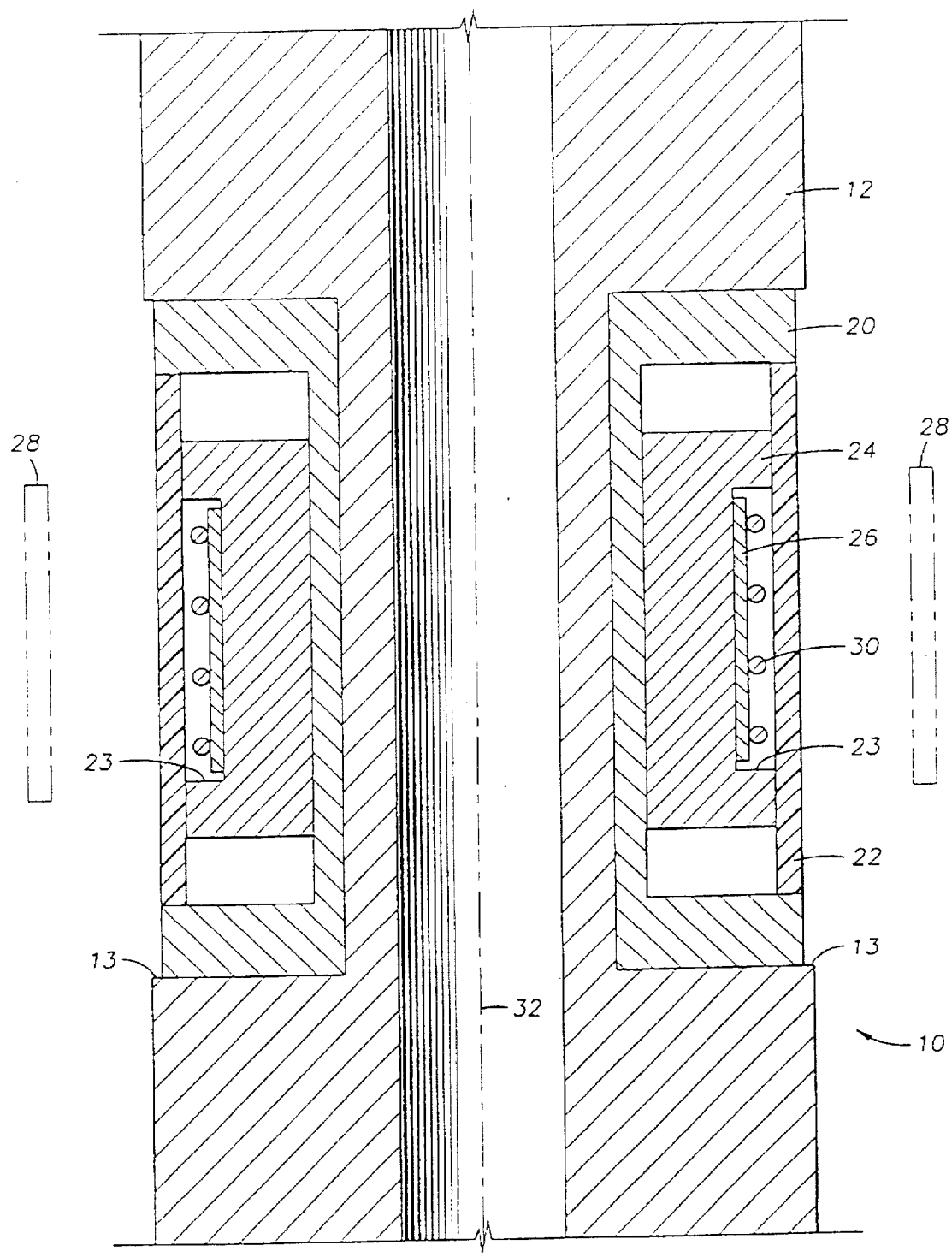
FIG. 2 shows a cross-sectional view of the apparatus of the preferred embodiment of the present invention.

The portion of the instrument 10 which includes sensing apparatus for making nuclear magnetic resonance (NMR) measurements of the earth formation can be better understood by referring to FIG. 2. FIG. 2 shows a cross-section of the instrument 10 wherein the NMR sensing apparatus is disposed. The NMR portion of the instrument 10 can be mounted in an annular recess 13 formed into one of the drill collars 12. The drill collar 12 is preferably made from a substantially non-ferromagnetic material such as monel. A soft iron flux closure 20 is inserted into the annular recess 13. The flux closure 20 can be formed from two semi-cylindrical sections which when assembled cover substantially the entire circumference of the annular recess 13 along the length of the flux closure 20. The flux closure 20 is included so that a substantially radially magnetized permanent magnet 24, disposed on the outer radial surface of the flux closure 20 will have suitable directional orientation of its magnetic field. The structure of the magnet 24 and the nature of its magnetic field will be further explained.

The magnet 24 can be made from a hard ferrite or other non-conductive permanent magnet material. The magnet 24 can be formed from half-cylinders as is the flux closure 20, or can be formed from a plurality of radial segments as will be further explained. The magnet 24 can include a recess 23 in its exterior surface. The recess 23 substantially circumscribes the exterior surface of the magnet 24 and is included to provide a space for mounting a soft ferrite 26 thereon.

The soft ferrite 26 preferably is formed from a material having high magnetic permeability. An antenna coil 30 can be wound around the exterior surface of the ferrite 26. In the present embodiment of the invention, the annular recess 13, the flux closure 20, the magnet 24, the ferrite 26 and the antenna 30 are preferably axially symmetric about the central axis 32 of the instrument 10.

The flux closure 20, magnet 24, ferrite 26 and antenna coil 30 are preferably enclosed with a protective cover 22. The cover 22 is intended to protect the enclosed components from damage caused by contact with the drilling mud (4 in FIG. 1) and the wall of the wellbore (2 in FIG. 1). The cover 22 can be formed from fiberglass, ceramic or other non-conductive, non ferromagnetic material having suitable mechanical properties.

The antenna coil 30 can be connected to circuitry (not shown in FIG. 2) for energizing the coil with radio frequency (RF) electrical pulses, and for receiving an induced NMR signal generated in a substantially cylindrical region 28 (hereinafter called the "sensitive volume") of the earth formation (14 in FIG. 1) radially separated from the axis 32 by a predetermined distance depending on the frequency of the RF pulses and the amplitude gradient of the magnetic field induced by the magnet 24. Circuitry which can perform the required RF pulse generation and NMR signal reception functions is described, for example in U.S. Pat. No. 4,710,713 issued to Taicher et al. The circuitry described in the Taicher et al '713 patent is meant to serve only as an example and is not meant to be an exclusive representation of circuitry which will perform the required functions of the present invention.

The antenna coil 30 is preferably wound so that turns of the antenna coil 30 lie in planes substantially perpendicular to the axis 32. When the RF pulses are conducted through the antenna coil 30, the RF magnetic field thus generated will have magnetization direction substantially parallel to the axis 32 within the sensitive volume 28. The sensitive volume 28, as previously explained, is a portion of the earth formations (14 in FIG. 1) in which the nuclear magnetic resonance condition is established and from which the NMR measurement originates. The significance of the magnetization direction of the RF magnetic field will be further explained.

A better understanding of the construction of the magnet 24 according to the present invention can be obtained by referring to FIG. 3A, which is a side view of the magnet 24. The magnet 24 can be composed of a series of axially magnetized cylinders, shown as 24A–24F. The magnetization direction of each cylinder is indicated by arrows on each cylinder. A particular feature of the axially magnetized cylinders is that the magnetization of each cylinder is proportional in magnitude to its axial distance from the center plane 24P of the magnet 24, and the magnetization is directed toward the center plane 24P. For example, uppermost cylinder 24A is shown as having a large magnetization directed downwardly towards the center plane 24P. Correspondingly opposite is lowermost cylinder 24F which has substantially equal strength magnetization to uppermost cylinder 24A but its magnetization is directed upwardly towards the center plane 24P. Successively more weakly magnetized pairs of cylinders, such as 24B/24E and 24C/24D are disposed successively closer to the center plane 24P. The resulting total magnetization of the magnet 24 shown in FIG. 3A is substantially radially outward (or inward) from the axis (shown as 32 in FIG. 2). The static magnetic field generated by the magnet 24 is also substantially rotationally symmetric about the axis (32 in FIG. 2), is substantially perpendicular to the axis (32 in FIG. 2), and at radial distances less than the axial length of the magnet decreases in field strength as the inverse of the radial distance from the magnet 24. The term "rotationally symmetric" as used in the description of the present invention indicates that at any particular radial distance from the cylindrical center of the magnet 24 (which is typically collocated with the axis 32), the amplitude of the magnetic field is substantially the same for any angular position about the center of the magnet 24. Explained alternatively, at any fixed radial distance relative to the cylindrical center of the magnet, if the magnet 24 is rotated about its center (collocated with the axis 32), the magnetic field strength does not change appreciably.

FIG. 3B shows a plan view of one of the cylinders, such as 24A. Each cylinder is preferably divided into half-cylinders so that the cylinder may be conveniently assembled to the drill collar (12 in FIG. 1). The magnet 24 shown in FIG. 3A does not require the use of the flux closure (20 in FIG. 2), and so can be assembled directly to the wall of the recess (13 in FIG. 1) in the drill collar (12 in FIG. 1).

An alternative configuration of the magnet 24 can be observed by referring to FIG. 4A, which shows a plan view of the alternative magnet 24. The magnet 24 can be constructed from a plurality of radial segments 34 of a cylinder, which when assembled form the substantially cylindrical annular magnet 24. Each segment 34 can be magnetized substantially uniformly along its length (parallel to the axis—32 in FIG. 2) and in a direction indicated by the arrows on each segment 34. The magnetization direction of each segment 34 can be substantially radially outward from the axis (32 in FIG. 2) as the segments 34 are assembled to form an annular cylinder. It is to be explicitly understood that the term "radially outward" as it concerns the magnetization direction of the segments 34 is used only for convenience of this description of the magnet 24, and is not to be construed as a limitation on the structure of the magnet 24. The actual direction of magnetization of the segments 34, as being radially outward from or radially inward towards the axis 32, is not important to the structure of the magnet 24. An assembled view of the alternative magnet 24 can be observed by referring to FIG. 4B. It is important to note that the alternative magnet 24 shown in FIG. 4B requires the use of the flux closure (shown as 20 in FIG. 2) to provide a static magnetic field which is substantially perpendicular to the axis (32 in FIG. 2), substantially rotationally symmetric about the axis (32 in FIG. 2) and has substantially uniform field strength along the axis (32 in FIG. 2).

Figure 5:
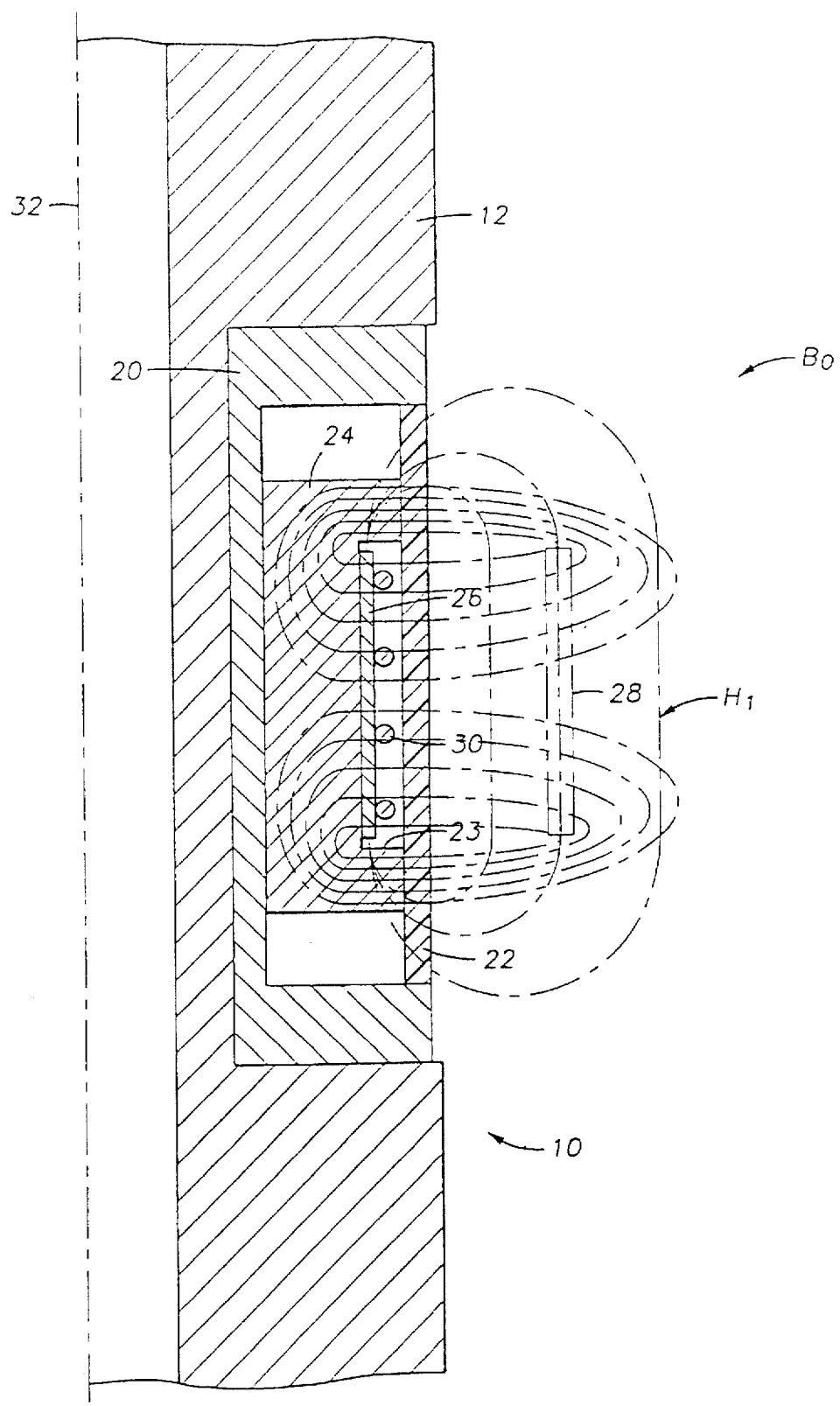
FIG. 5 shows the relative orientation of the static and radio frequency magnetic field generated by the apparatus of the present invention.

The significance of the embodiments of the magnet 24 and the antenna coil 30 of the present invention can be better understood by referring to FIG. 5. The instrument 10 in FIG. 5 includes the magnet 24 as shown in FIG. 4B, and therefore includes the flux closure 20, but it is to be explicitly understood that the function of the first embodiment of the magnet 24, which does not require the flux closure 20, is also explained by the following discussion.

The magnet 24 generates, as previously described, a static magnetic field which has substantially uniform field strength along the axis 32, is substantially radially symmetric around the axis 32 and is substantially perpendicular to the axis 32 within the sensitive volume 28. The magnetization direction of the static magnetic field is indicated by field lines designated by $B_0$. When the antenna coil 30 is energized by the RF electrical pulses, an RF magnetic field is generated. The RF magnetic field direction is designated by $H_1$. As is understood by those skilled in the art, a nuclear magnetic resonance condition is created where the RF magnetic field frequency substantially matches the nuclear spin precession frequency. The nuclear spin precession frequency is directly proportional to the static magnetic field strength. In the present embodiment of the invention, the resonance condition can be created within the sensitive volume 28. The radius of the sensitive volume 28 can be selected by appropriate choice of the RF magnetic field frequency so that the RF magnetic field direction $H_1$ within the sensitive volume 28 is substantially parallel to the axis 32, and is therefore substantially perpendicular to the static magnetic field $B_0$. The sensitive volume 28 thus generated is substantially cylindrical and symmetric about the axis 32.

A particular advantage of the present invention over NMR well logging apparatus of the prior art is that in the present invention the static and RF magnetic fields, are rotationally symmetric about the axis 32. Rotational symmetry provides a measurement which is relatively immune to error caused by axial rotation of the instrument 10. The instrument 10 according to the present invention is particularly well suited for use in MWD applications where the instrument 10 is highly likely to be used while undergoing axial rotation.

It is to be understood that the structure of the NMR well logging apparatus disclosed herein may also be built on a sonde adapted to be conveyed into the wellbore at one end of an armored electrical cable. While the embodiment disclosed herein is particularly adapted to be used in a measurement-while-drilling instrument, the present invention may also be adapted to be used with other types of conveyances for well logging instruments known in the art.

The description of the embodiment disclosed herein is meant to serve only as an example of apparatus which will fulfill the spirit of the present invention. Accordingly, the invention should be limited in scope only by the following claims.

What is claimed is:

1. A nuclear magnetic resonance sensing apparatus, comprising:

a magnet for inducing a static magnetic field in materials to be analyzed, said static magnetic field substantially rotationally symmetric about a longitudinal axis of said magnet, said static magnetic field substantially perpendicular to said longitudinal axis, said static magnetic field having substantially equal amplitude along said longitudinal axis;

means for generating a radio frequency magnetic field in said materials to be analyzed, said radio frequency magnetic field substantially rotationally symmetric about said longitudinal axis, said radio frequency magnetic field substantially parallel to said longitudinal axis within a sensitive volume containing said materials to be analyzed; and means for receiving a nuclear magnetic resonance signal from said sensitive volume.

2. The apparatus as defined in claim 1 wherein said magnet comprises a plurality of radial cylinder segments assembled into an annular cylinder, said cylinder segments each magnetized so that said annular cylinder includes substantially uniform magnetization in a direction radially outward from and substantially perpendicular to said longitudinal axis.

3. The apparatus as defined in claim 2 further comprising a flux closure disposed inside said annular cylinder.

4. The apparatus as defined in claim 1 wherein said magnet comprises gradient magnetization increasing along said longitudinal axis corresponding to a distance along said longitudinal axis from a center plane of said magnet.

5. The apparatus as defined in claim 4 wherein said magnet comprises a plurality of axially magnetized annular cylinders arranged along said longitudinal axis of said magnet, each of said axially magnetized annular cylinders having a magnetization corresponding to said distance from said center plane of each said cylinder.

6. The apparatus as defined in claim 1 wherein said means for generating comprises an antenna coil wound so that turns of said coil lie in planes substantially perpendicular to said longitudinal axis.

7. The apparatus as defined in claim 6 further comprising a high magnetic permeability ferrite disposed inside said antenna coil.

8. The apparatus as defined in claim 1 wherein said magnet, said means for generating and said means for receiving are disposed on a drill collar.

9. A nuclear magnetic resonance well logging apparatus adapted for measurement-while-drilling, comprising:

a drill collar adapted to be connected within a drilling assembly;

a magnet disposed on said drill collar for inducing a static magnetic field in materials to be analyzed, said static magnetic field substantially rotationally symmetric about a longitudinal axis of said magnet, said static magnetic field substantially perpendicular to said longitudinal axis, said static magnetic field having substantially equal amplitude along said longitudinal axis;

means for generating a radio frequency magnetic field in said materials to be analyzed, said means for generating disposed on said drill collar, said radio frequency magnetic field substantially rotationally symmetric about said longitudinal axis and parallel to said longitudinal axis within a sensitive volume containing said materials to be analyzed; and means for receiving a nuclear magnetic resonance signal from said sensitive volume.

10. The apparatus as defined in claim 9 wherein said magnet comprises a plurality of cylinder segments assembled into an annular cylinder, said segments each magnetized so that said annular cylinder includes substantially uniform magnetization along said longitudinal axis and substantial rotational symmetry about said longitudinal axis.

11. The apparatus as defined in claim 10 further comprising a flux closure disposed within said annular cylinder.

12. The apparatus as defined in claim 9 wherein said magnet comprises gradient magnetization increasing along said longitudinal axis corresponding to a distance along said longitudinal axis from a center plane of said magnet.

13. The apparatus as defined in claim 12 wherein said magnet comprises a plurality of axially magnetized annular cylinders arranged along said longitudinal axis of said magnet, each of said axially magnetized annular cylinders having a magnetization corresponding to said distance from said center plane of each said cylinder.

14. The apparatus as defined in claim 9 wherein said means for generating comprises an antenna coil wound so that turns of said coil lie in planes substantially perpendicular to said longitudinal axis.

15. The apparatus as defined in claim 14 further comprising a high magnetic permeability ferrite disposed inside said antenna coil.

16. A method for nuclear magnetic resonance measurement, comprising:

inducing a static magnetic field in materials to be analyzed, said static magnetic field having substantially uniform field strength along a longitudinal axis, said static magnetic field substantially rotationally symmetric about said longitudinal axis and substantially perpendicular to said longitudinal axis;

generating a radio frequency magnetic field in said materials to be analyzed, said radio frequency magnetic field substantially rotationally symmetric about said longitudinal axis and substantially parallel to said longitudinal axis within a sensitive volume containing said materials to be analyzed; and receiving a nuclear magnetic resonance signal from said sensitive volume.

17. The method as defined in claim 16 wherein said materials to be analyzed include earth formations surrounding a wellbore drilled therethrough.

18. The method as defined in claim 17 further comprising repeating said steps of inducing said static magnetic field, generating said radio frequency magnetic field and receiving said nuclear magnetic resonance signal at a plurality of axial locations along said wellbore.

19. The method as defined in claim 18 wherein said plurality of axial locations are provided by moving a drilling assembly into said wellbore during the drilling thereof.

20. A method of logging a wellbore to determine nuclear magnetic resonance properties of earth formation surrounding said wellbore, comprising:

inducing a static magnetic field in said earth formations, said static magnetic field having substantially uniform field strength along a longitudinal axis, said static magnetic field substantially rotationally symmetric about said longitudinal axis and substantially perpendicular to said longitudinal axis;

generating a radio frequency magnetic field in said earth formations, said radio frequency magnetic field substantially rotationally symmetric about said longitudinal axis and parallel to said longitudinal axis within a sensitive volume positioned within said earth formations;

receiving a nuclear magnetic resonance signal from said sensitive volume.

21. The method as defined in claim 20 further comprising repeating said steps of inducing said static magnetic field, generating said radio frequency magnetic field and receiving said nuclear magnetic resonance signal at a plurality of axial locations along said wellbore.

22. The method as defined in claim 21 wherein said plurality of axial locations are provided by moving a drilling assembly into said wellbore during the drilling thereof.

23. The method as defined in claim 22 further comprising transmitting signals corresponding to measurements made during said step of receiving to equipment at the earth's surface by drilling mud pressure modulation telemetry.

* * * * *